United States Patent [19]

Hendrick ter Maat et al.

[11] Patent Number: 5,424,445
[45] Date of Patent: Jun. 13, 1995

[54] ALKOXYLATION PRODUCTS

[75] Inventors: Johan H. Hendrick ter Maat; Marion Meyer, both of Mannheim; Knut Oppenlaender, Ludwigshafen; Michael Zirnstein, Schriesheim; Walter Denzinger, Speyer; Lothar Franz, Mutterstadt, all of Germany

[73] Assignee: BASF Aktiengesellschaft, Ludwigshafen, Germany

[21] Appl. No.: 99,140

[22] Filed: Jul. 29, 1993

[30] Foreign Application Priority Data

Aug. 3, 1992 [DE] Germany .................. 42 25 619.4

[51] Int. Cl.⁶ .................. C07D 207/40; B01F 17/00; C07C 217/08; C07C 229/22
[52] U.S. Cl. .................. 548/543; 106/287.17; 106/287.2; 106/287.23; 106/287.25; 106/287.3; 106/493; 106/499; 548/520; 548/523; 564/199
[58] Field of Search .................. 548/543, 520, 523; 106/287.17, 287.2, 287.23, 287.25, 287.3, 493, 499

[56] References Cited

U.S. PATENT DOCUMENTS

| | | | |
|---|---|---|---|
| 2,170,111 | 8/1939 | Bruson | 260/293 |
| 2,189,397 | 2/1940 | Harris | 260/286 |
| 2,828,316 | 3/1958 | Pacini et al. | 260/301 |
| 4,026,719 | 5/1977 | Simic | 106/287.23 |
| 4,684,409 | 8/1987 | Hodge et al. | 106/287.23 |
| 4,769,078 | 9/1988 | Tso | 106/287.25 |
| 4,958,032 | 9/1990 | O'Lenick, Jr. | 548/543 |
| 4,979,993 | 12/1990 | Okamoto et al. | 106/287.23 |
| 5,112,404 | 5/1992 | Sommer et al. | 106/442 |
| 5,144,060 | 9/1992 | Morita et al. | 560/170 |
| 5,320,673 | 6/1994 | Carpenter et al. | 106/287.23 |

FOREIGN PATENT DOCUMENTS

| | | |
|---|---|---|
| 107089 | 5/1984 | European Pat. Off. |
| 182669 | 5/1986 | European Pat. Off. |
| 1087415 | 10/1967 | United Kingdom |
| 1342746 | 1/1974 | United Kingdom |

OTHER PUBLICATIONS

*Chem. Abst.*, vol. 103, No. 22, Dec. 2, 1985 (English abstract of JP-A 6089458).

*Primary Examiner*—David B. Springer
*Attorney, Agent, or Firm*—Keil & Weinkauf

[57] ABSTRACT

Alkoxylation products which are suitable as dispersants and are of the general formula I $$(R^1)_x-A+(B-O)_n-B-NR^2R^3]_y$$

where
A is oxygen or —CO—O— when x and y are each 1 or is nitrogen when $x+y=3$,
B is ethylidene or 1,2-propylidene,
Z is one of the groups

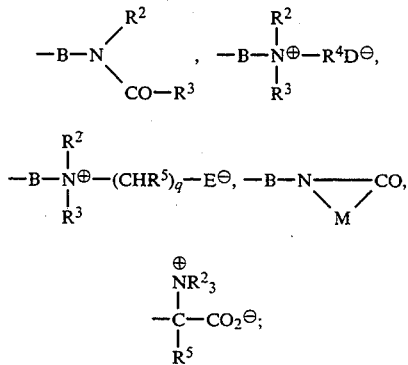

$D^\ominus$ is formate, acetate, propionate or hydroxide,
$E^\ominus$ is carboxylate or sulfonate,
M is a bridge group for completion of a pyrrolidone, succinimide or maleimide ring to give a group

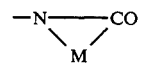

n is from 1 to 50,
q is from 1 to 4, (Abstract continued on next page.)

x and y are each 1 or 2, with the proviso that $x+y \leq 3$,
$R^1$ is $C_8$–$C_{30}$-alkyl or, when A is oxygen, is $C_4$–$C_{12}$-alkyl-substituted phenyl,
$R^2$, $R^3$ and $R^4$ are each hydrogen, methyl or ethyl and
$R^5$ is hydrogen or methyl,
a process for their preparation, their use for dispersing finely divided solids in flowable media, and formulations containing the alkoxylation products.

4 Claims, No Drawings

ALKOXYLATION PRODUCTS

The present invention relates to novel alkoxylation products which are suitable as dispersants and are of the general formula I

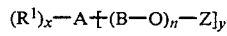  I where
A is oxygen or —CO—O— when x and y are each 1 or is nitrogen when x+y=3,
B is ethylene or 1,2-propylene,
Z is one of the groups

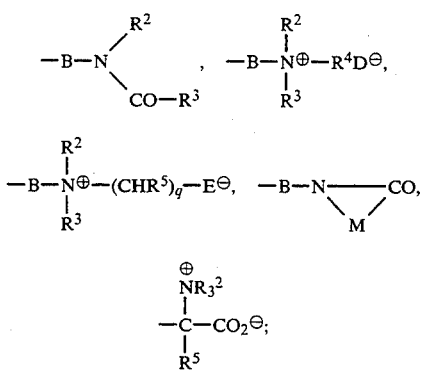

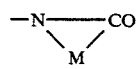

$D^{\ominus}$ is formate, acetate, propionate or hydroxide,
$E^{\ominus}$ is carboxylate or sulfonate,
M is a bridge group for completion of a pyrrolidone, succinimide or maleimide ring to give a group $$-N\underset{M}{\overset{\diagdown\phantom{M}\diagup}{\phantom{-}}}CO$$

n is from 1 to 50,
q is from 1 to 4,
x and y are each 1 or 2, with the proviso that $x+y \leq 3$,
$R^1$ is $C_8$-$C_{30}$-alkyl or, when A is oxygen, is $C_4$-$C_{12}$-alkyl-substituted phenyl,
$R^2$, $R^3$ and $R^4$ are each hydrogen, methyl or ethyl and
$R^5$ is hydrogen or methyl.

The present invention furthermore relates to a process for the preparation of the alkoxylation product I, their use for dispersing finely divided powders in flowable media and furthermore formulations which contain the compounds I.

For a large number of industrial processes, it is essential to convert finely divided powders into stable dispersions. Dispersants are used for dispersing in a medium in which the powders are insoluble. Since the requirements which the dispersants have to meet differ greatly owing to the large number of different powders and possible dispersing media, uneconomical, individual solutions for dispersing problems, ie. a certain dispersant for a specific combination of powder and dispersing medium, are widespread.

GB-A 1 342 746 discloses polymers of hydroxycarboxylic acids and their use as dispersants for a number of pigments in organic solvents. However, these dispersants are unsuitable for use in water.

Furthermore, DE-A-40 26 965 discloses castable molding materials which, in addition to sinterable powders and organic solvents from the series consisting of the alkanes, ethers, esters and ketones, contain dispersants of the general formula I'

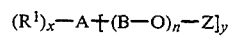  I

These compounds differ from the novel compounds I in the polar terminal group Z'.

Z' is hydrogen, sulfo, a phosphoric acid radical, carboxylate, amino or amido having a free amino component.

These dispersants are suitable for the stated organic dispersing media but are unsatisfactory in alcohol-and water-containing media.

In addition to homogeneous distribution of the powders in the dispersions, a dispersant should furthermore permit a very high content of the particular powder in the dispersions, since the processing (for example by milling) of concentrated dispersions is generally more economical than the processing of dispersions having a low powder content, provided that the viscosity does not exceed certain limits.

It is an object of the present invention to provide compounds which have broad dispersing properties, ie. disperse many different powders in various media. They should also permit a high powder content or enable the preparation of very low-viscosity formulations at a constant powder content.

We have found that this object is achieved by the alkoxylation products defined at the outset.

We have also found a process for the preparation of the compounds I and use of I as dispersants for finely divided powders in flowable media. We have furthermore found formulations which contain a compound I in addition to finely divided powders and flowable media.

A is preferably oxygen but may furthermore be —CO—O— when x and y are each 1 or nitrogen when x+y is 3,
B is preferably ethylene but may furthermore be 1,2propylene,
Z is one of the groups

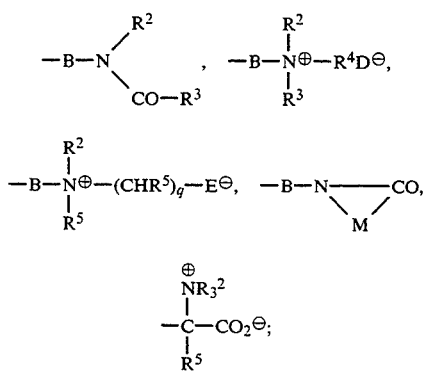

the following groups being preferred:

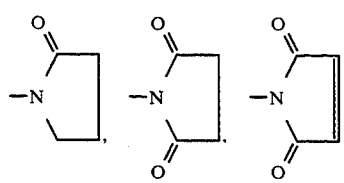

-continued
—CH$_2$CH$_2$N$^\oplus$R$^2$R$^3$—CH$_2$—CO$_2^\ominus$,

D$^\ominus$ is preferably acetate but may furthermore be formate, propionate or hydroxide, E$^\ominus$ is preferably carboxylate but may furthermore be sulfonate, M is a bridge group for completion of a pyrrolidone, succinimide or maleimide to give a group

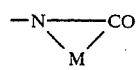

and n is from 1 to 50, preferably from 2 to 25, q is from 1 to 4, preferably 1, and x and y are each 1 or 2, with the proviso that $x+y \leq 3$, R$^1$ is preferably C$_8$–C$_{30}$-alkyl, in particular C$_{12}$–C$_{18}$-alkyl, including in particular mixtures of C$_{13}$/C$_{15}$-oxo alcohol radicals and C$_{12}$/C$_{14}$ and C$_{16}$/C$_{18}$ fatty alcohol radicals, or, where A is oxygen, R$^1$ is C$_4$–C$_{12}$-alkyl-substituted phenyl, preferably tert-butyl-, isooctyl- or isononylphenyl, R$^2$, R$^3$ and R$^4$ are each preferably hydrogen or methyl but may furthermore be ethyl and R$^5$ is hydrogen or methyl.

The compounds I are alkyl oxide or polyalkylene oxide derivatives having the radicals (R$^1$)$_x$—A— and —Z as terminal groups.

Aminated alkoxyalcohols II

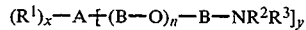

or oxidized alkoxyalcohols III

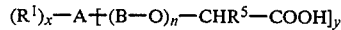

are advantageously used as starting materials for the synthesis of I.

If A is oxygen, the compounds II are obtained by alkoxylation of an alcohol R$^1$—OH with an alkylene oxide and further amination, for example according to U.S. Pat. No. 3 440 029. Complete methylation at the nitrogen atom is possible, if desired, by reaction with formic acid and formaldehyde.

If A is —CO—O—, the synthesis of II is carried out similarly to the reaction described above with carboxylic acid R$^1$—COOH instead of an alcohol.

If A is nitrogen, aminated fatty alcohols, which are commercially available or obtainable by known methods, are alkoxylated and are aminated as described above. The nitrogen atom may carry two alkyl radicals and hence one alkylene oxide unit or one alkyl radical and two alkyene oxide units.

The compounds III are obtainable by oxidation instead of amination of the alkoxyalcohols described above. Some of them are also commercially available.

In the intermediate compounds II or III obtained in this manner, the polar terminal groups Z are introduced by subsequent reactions.

Specifically, a compound II in which at least one of the radicals R$^2$ or R$^3$ is hydrogen is reacted in a known manner with the carboxylic acid R$^3$—COOH to give the amide.

The reaction of a compound II having a C$_1$–C$_3$-carboxylic acid under less drastic reaction conditions than in the above case leads to salts of C$_1$–C$_3$-carboxylic acids.

The compounds II may furthermore be reacted with hydrochloric acid to give the corresponding chlorides, which can be converted into ammonium hydroxides by reaction with silver hydroxide.

Novel betaines can be obtained if the compound II reacts with an ω-chloro-C$_2$–C$_4$-carboxylic acid or an alkali metal salt thereof.

The compound II having a terminal NH$_2$ group can be converted by reaction with γ-butyrolactone, succinic anhydride or maleic anhydride into a compound I in which

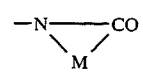

is a N-pyrrolidone, N-succinimide or N-maleimide group.

Finally, the α-halogenation of a compound III and subsequent substitution by ammonia or an amine, followed by alkylation at the nitrogen, for example with an alkyl iodide, leads to a betaine in which Z is —CR$^5$(N$^\oplus$R$^2_3$)CO$_2^\ominus$.

The novel compounds I are used for dispersing finely divided solids in a flowable medium.

Such solids are preferably oxidic or non-oxidic ceramic powders and metal powders, in addition to inorganic and organic pigments.

Examples of oxidic powders include MgO, TiO$_2$, ZrO$_2$, CrO$_2$, Y$_2$O$_3$, Al$_2$O$_3$ and Fe$_2$O$_3$, as well as mixed oxides, such as BaTiO$_3$, aluminum silicates, stabilized zirconium oxides and ferrites.

Suitable non-oxidic ceramic powders include SiC, Si$_3$N$_4$, BN, AlN and WC. Graphite is also suitable.

Examples of metals are Fe, Ni, Cr, Mo and the metalloid Si.

Finely divided means that the mean particle sizes are in general from 0.1 to 50 μm.

Flowable media include fluids which are liquid at room temperature, such as water or organic solvents, such as alcohols, ethers, ether alcohols, esters, aliphatic and aromatic hydrocarbons, halohydrocarbons, amines, amides and nitro compounds. Mixtures of these substances are of course also be used.

Substances which are flowable only at temperatures higher than room temperature are also suitable, for example waxes and thermoplastic polymers, such as polymethyl methacrylate, polystyrene, polyamides, poloxymethylene, polyethylene and polyesters. Solutions of monomers or polymers are also suitable.

Novel formulations are obtainable from the above-mentioned finely divided solids, the flowable media and compounds of the formula I.

These generally contain:

20–99.8% by weight of finely divided solids, 0.1–80% by weight of free-flowing medium and 0.1–20, preferably 0.2–5, % by weight of compound I.

The formulations may furthermore contain assistants and additives conventionally used for the particular application, for example plasticizers, water retention substances, mold release agents, UV stabilizers and corrosion inhibitors.

The novel formulations are prepared in a conventional manner. Thus, it has proven particularly useful on the small scale to carry out dispersing using ultrasonic waves, by adding the solid to the dispersing medium and dispersant in an ultrasonic bath.

For larger batches, it is advantageous to rely on milling, for example in a ball mill, or to use kneaders. Plastics having a high filler content can advantageously be prepared in an extruder. It is possible to use the powder and dispersant separately or granules of the powder coated with the dispersant. The granules can be prepared by mixing the powder and dispersant in a solvent and then removing the solvent completely.

The novel compounds I permit the dispersing of various powders in polar, moderately polar and slightly polar solvents. High powder contents are achieved and the dispersions have a relatively low viscosity at constant powder contents.

EXAMPLES

1. Preparation of the compounds I

Example 1 (Dispersant A)
$(C_{13}/C_{15}\text{-Alkyl})-O-(CH_2CH_2O)_6-CH_2CH_2N^{\oplus}H_2(CH_3)CH_3CO_2^{\ominus}$ An ethoxylated $C_{13}/C_{15}$-oxo alcohol (ratio of $C_{13}$ to $C_{15}$ 2:1) having a degree of ethoxylation of 7 was aminated with methylamine. 11.2 g of acetic acid were added to 100 g of the amination product thus obtained. Excess acetic acid was removed at 80° C. under reduced pressure, and a yellow liquid remained.

Example 2 (Dispersant B)
$(C_{13}/C_{15}\text{-Alkyl})-O-(CH_2CH_2O)_6-CH_2CH_2N^{\oplus}(CH_3)_2CH_2CO_2^{\ominus}$ 100 g of the amination product prepared under Example 1 were refluxed with 43 g of concentrated formic acid and 16.8 g of a 40% strength by weight formalin solution for 2 hours, neutralized, distilled azeotropically with toluene and filtered. The solvent was removed. 50 g of the slightly yellow liquid thus obtained were refluxed for 5 hours with 13.8 g of an aqueous 50% strength by weight solution of the sodium salt of chloroacetic acid. After the water and salt had been separated off, a brown viscous liquid remained.

Example 3 (Dispersant C) $(C_{16}/C_{18}\text{-Alkyl})-O-(CH_2CH_2O)_{10}-CH_2CH_2N^{\oplus}(CH_3)_2CH_2CO_2^{\ominus}$ An ethoxylated $C_{16}/C_{18}$-fatty alcohol (ratio of $C_{16}$ to $C_{18}$ 0.5:1) having a degree of ethoxylation of 11 was aminated with methylamine similarly to Example 1, methylated similarly to Example 2 and converted into the betaine

Example 4 (Dispersant D)

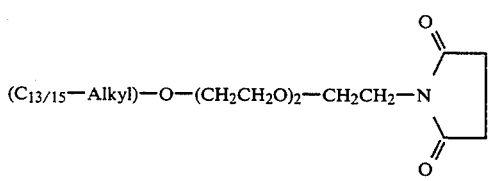

A $C_{13}/C_{15}$-oxo alcohol (ratio of $C_{13}$ to $C_{15}$ 2:1) having an average degree of ethoxylation of 3 was aminated using an excess of ammonia. 29 g of succinic anhydride were added to 100 g of the amination product thus obtained. Reduced pressure from a water pump was applied for 2 hours at 150° C. A dark brown liquid was obtained.

Example 5 (Dispersant E)

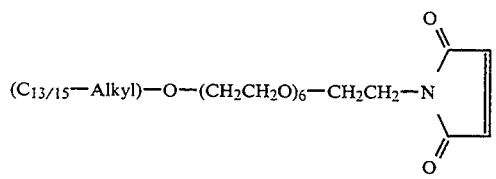

An ethoxylated $C_{13}$–$C_{15}$-fatty alcohol (ratio of $C_{13}$ to $C_{15}$ 2:1) having a degree of ethoxylation of 7 was aminated with ammonia. 100 g of the colorless liquid thus obtained were heated with 19 g of maleic anhydride for 2 hours at 160° C., reduced pressure from a water pump being applied. A dark brown liquid was obtained.

Example 6 (Dispersant F)

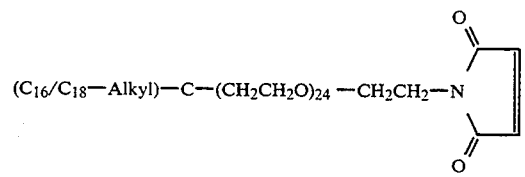

An ethoxylated $C_{16}$–$C_{18}$-fatty alcohol (ratio of $C_{16}$ to $C_{18}$ 0.5:1) having a degree of ethoxylation of 25 was aminated with ammonia. 100 g of the colorless wax thus obtained were reacted with 7.2 g of maleic anhydride similarly to Example 5. A golden brown wax was obtained.

Example 7 (Dispersant G)

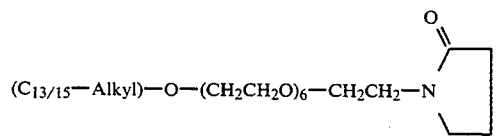

100 g of the aminated product according to Example 5 were heated with 17 g of γ-butyrolactone for 5 hours at 180° C. A pale brown liquid was obtained.

Example 8 (Dispersant H)

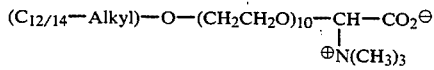

1 g of red phosphorus and 100 g of bromine were added to 100 g of an ethoxylated $C_{12}$–$C_{14}$-fatty alcohol (ratio of $C_{12}$ to $C_{14}$ 2:1) having a degree of ethoxylation of 10 and a terminal carboxyl group. After 1 week at 50° C., all volatile components were removed. 100 ml of a 20% strength by weight aqueous ammonia solution were added to the residue. After 4 days, the water was removed azeotropically, filtration was carried out and volatile components were stripped off. 100 g of methyl iodide were added to the product in 200 ml of nitromethane. After 30 minutes, all volatile components were removed at 80° C. A pale brown paste remained.

2. Dispersions having a high powder content 50 ml of a solvent and the amount of dispersant stated below were initially taken and stirred, and the powders stated below were added a little at a time while treating with ultrasonics in an ultrasonic bath. The addition was terminated when the batch was no longer stirrable.

The larger the amount of powder which can be incorporated into the dispersion, the more efficient is the dispersant used.

The following batches were used:

| Powder | Particle size [μm] | Amount of dispersant [g] |
|---|---|---|
| ZrO₂ (5% by weight of Y₂O₃) | 0.3 | 6 |
| SiC | 0.6 | 3.2 |
| Y₂O₃ | 0.4 | 5 |
| Si₃N₄ | 0.7 | 3 |
| Al₂O₃ | 0.7 | 4 |

2.1 Weakly polar solvents

The Table shows the amounts of powder which were stirrable in 50 ml of solvent with the stated amount of dispersant.

| Solvent | Powder | Dispersant | Amount of powder [g] according to the invention |
|---|---|---|---|
| n-Octane | ZrO₂ | D | 260 |
| n-Octane | SiC | A | 160 |
| n-Octane | Y₂O₃ | C | 190 |
| Toluene | SiC | E | 160 |
| Toluene | Y₂O₃ | E | 205 |

2.2 Moderately polar solvents

| Solvent | Powder | Dispersant | Amount of powder [g] according to the invention |
|---|---|---|---|
| Dimethylacetamide | Al₂O₃ | E | 200 |
| | Y₂O₃ | E | 195 |
| THF | Y₂O₃ | C | 180 |
| Butyl acetate | ZrO₂ | E | 250 |
| | Y₂O₃ | E | 195 |

2.3 Polar solvents

| Solvent | Powder | Dispersant | Amount of powder [g] according to the invention |
|---|---|---|---|
| Water | Si₂N₄ | C | 145 |
| | Al₂O₃ | C | 145 |
| Butylglycol | ZrO₂ | E | 300 |
| | SiC | B | 160 |
| n-Butanol | SiC | E | 155 |
| | | H | 160 |
| | Y₂O₃ | E | 195 |
| Isopropanol | Al₂O₃ | E | 200 |
| | SiC | B | 150 |
| | Y₂O₃ | E | 165 |

2.4 Viscosity measurement

In these experiments, 200 g of Al₂O₃ powder having a mean particle size of 0.7 μm were added to 50 ml of solvent and 4 g of novel dispersant and were dispersed by stirring in an ultrasonic bath. The viscosity was determined at a shear rate of 1000 s⁻¹ using a rotation viscometer.

The lower the viscosity at a constant powder content of the dispersion, the more efficient is the dispersant used.

| Solvent | Dispersant | Viscosity [mPa·s] according to the invention |
|---|---|---|
| n-Octane | E | 38 |
| | G | 33 |
| Toluene | E | 34 |
| THF | E | 78 |
| | F | 32 |
| Butyl acetate | F | 43 |
| | H | 39 |
| Butylglycol | E | 97 |
| | F | 122 |

2.5 Viscosity on extrusion

Granules I were prepared from ZrO₂ particles which had been coated with the dispersant E. For this purpose, 363 g of ZrO₂ powder (stabilized with 5.2% by weight of Y₂O₃, particle size 0.3 μm), 5.45 g of dispersant E ant 140 ml of n-octane were milled for 2 hours at 2200 min⁻¹ in a stirred ball mill. The dispersion thus obtained was evaporated to dryness at 100° C. under reduced pressure.

300 g of the granules were added to 67 g of polyoxymethylene which was dissolved in 300 ml of diethylene glycol dimethyl ether at 162° C., and the mixture was freed from the solvent in about 30 seconds under reduced pressure with foaming. The foamed product was comminuted.

To measure the viscosity, the formulation was introduced into a cylinder at 170° C. and extruded through an interchangeable nozzle at a constant ram speed.

The melt of the granules was still extrudable through a nozzle having 10 holes of 70 μm diameter. The fibers thus produced reached a length of several meters.

We claim:

1. A dispersant composition comprising 0.1–20% by weight of a dispersant of the formula I $$(R^1)_x-A+(B-O)_n-Z]_y$$

where
A is oxygen or —CO—O— when x and y are each 1 or is nitrogen when x+y=3,
B is ethylene or 1,2-propylene,
Z is one of the groups

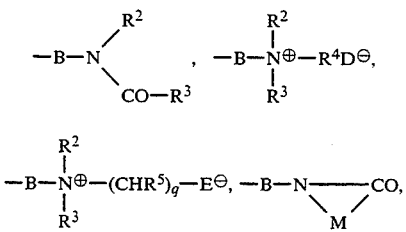

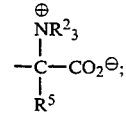

D⊖ is formate, acetate, propionate or hydroxide,
E⊖ is carboxylate or sulfonate,
M is a bridge group for completion of a pyrrolidone, succinimide or maleimide ring to give a group

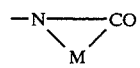

n is from 1 to 50, q is from 1 to 4, x and y are each 1 or 2, with the proviso that $x+y \leq 3$, $R^1$ is $C_8$–$C_{30}$-alkyl or, when A is oxygen, is $C_4$–$C_{12}$-alkyl-substituted phenyl, $R^2$, $R^3$ and $R^4$ are each hydrogen, methyl or ethyl, and $R^5$ is hydrogen or methyl;

20–99.8% by weight of solids having a particle size of from 1 to 50 μm, which solids are at least one member selected from the group consisting of oxidic ceramic powders, non-oxidic ceramic powders, oxidic metal powders, non-oxidic metal powders, and organic pigments; and 0.1–80% by weight of a flowable medium which comprises at least one fluid which is liquid at room temperature.

2. The dispersant composition of claim 1 wherein in the dispersant compound of formula I, A is oxygen, B is ethylene, $R^1$ is $C_{16}$-alkyl, Z is

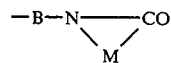

M, is a bridge group for completion of a maleimide ring n is 8, x is 1, and y is 1; the flowable medium is n-octane; and the solid is $Al_2O_3$.

3. A process for dispersing finely divided solids in a flowable medium, which comprises mixing the components as defined in claim 10 in the following proportions:

a) 20–99.8% by weight of at least one solid
b) 1–80% by weight of the flowable medium
c) 0.1 to 20% of the dispersant.

4. A process for dispersing finely divided solids in a flowable medium, which comprises: mixing 20–99.9% by weight of $Al_2O_3$ with 1–80% by weight n-octane and 0.1–20% by weight of the dispersant of claim 2.

* * * * *